United States Patent [19]

Biegeleisen

[11] Patent Number: 4,835,191
[45] Date of Patent: May 30, 1989

[54] METHODS FOR PREVENTION OF POST-INFLAMMATORY HYPERPIGMENTATION

[76] Inventor: Ken P. Biegeleisen, 91 Hudson Ave., Irvington, N.Y. 10533

[21] Appl. No.: 93,072

[22] Filed: Sep. 1, 1987

Related U.S. Application Data

[63] Continuation of Ser. No. 605,799, May 1, 1984, abandoned.

[51] Int. Cl.⁴ .................. A61K 31/045; A61K 31/10; A61K 7/40
[52] U.S. Cl. .................................. 514/708; 514/730; 514/947; 424/59; 424/60
[58] Field of Search .................. 424/59, 62; 514/947, 514/708, 730

[56] References Cited

U.S. PATENT DOCUMENTS

| | | |
|---|---|---|
| 2,274,725 | 1/1970 | Meeker et al. |
| 2,376,884 | 10/1973 | Schwenk et al. |
| 2,377,188 | 7/1979 | Schwenk et al. |
| 3,060,097 | 10/1962 | Fellows ................................. 424/62 |
| 3,527,864 | 9/1970 | MacMillen et al. |
| 3,549,770 | 12/1970 | Herschler et al. |
| 3,551,554 | 12/1970 | Herschler ............... 424/59 |
| 3,678,156 | 7/1972 | MacMillen et al. |
| 3,711,606 | 1/1973 | Herschler. |
| 3,740,420 | 6/1973 | Herschler et al. |
| 4,136,166 | 1/1979 | Barnett et al. |

OTHER PUBLICATIONS

Bleenan "Skin Bleaching Preparations" J. Soc. Cosm. Chem. 28 407-412 (1977) pp. 407-412.
Okuno et al "Dimethyl Terephthalate Compositions" cited in Chem. Abstracts vol. 78, 1983 147588j.
The Merck Index 9th ed. Dimethyl Sulfoxide (p. 433) and Hydroquinine (p. 635).

*Primary Examiner*—Ronald W. Griffin
*Assistant Examiner*—Jacqueline M. Stone
*Attorney, Agent, or Firm*—Pennie & Edmonds

[57] ABSTRACT

Compositions of hydroquinone and an aliphatic sulfoxide of the formula

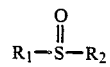

wherein $R_1$ and $R_2$ are alkyl, substituted alkyl, alkenyl, or hetero groups, along with appropriate pharmaceutical diluents, excipients, and/or adjuvants are disclosed. The preferred aliphatic sulfoxide is dimethyl sulfoxide, and the sulfoxide content can range between about 1 and 99 weight percent, preferably between about 25 and 90 weight percent. The hydroquinone content ranges between about 1 and 10 weight percent, preferably between about 1.5 and 5 weight percent.

Also disclosed are various methods for preventing, eliminating, or substantially reducing post-inflammatory hyperpigmentation by applying these compositions to hyperpigmented tissue of hyman or animal subjects as often as necessry to remedy or alleviate the hyperpigmentation.

6 Claims, No Drawings

METHODS FOR PREVENTION OF POST-INFLAMMATORY HYPERPIGMENTATION

This is a continuation of application Ser. No. 605,799, filed May 1, 1984 and now abandoned.

TECHNICAL FIELD

This invention relates to compositions for topical application to human or animal tissue and methods for preventing, eliminating, or substantially reducing post-inflammatory hyperpigmentation of such tissue.

BACKGROUND ART

Post-inflammatory hyperpigmentation is a condition wherein skin darkens or acquires a brown color after experiencing some type of trauma. This can result from the injection of chemicals into the skin, from skin burns, or even in some situations from bruises.

In the treatment of varicose veins or telangiectasis, for example, about three to four weeks after the veins are injected with a sclerosing solution, the purple colors of the veins disappear as the blood vessels dissolve. As these purple lines of the blood vessels are removed, they are replaced by brown lines due to post-inflammatory hyperpigmentation.

Hyperpigmentation can also be a manifestation of hormonal changes as in Addison's disease, pregnancy, or the use of anovulatory pills. Darkening may also result from increased melanogenesis, as is seen in hemochromatosis, or from silver deposits, as are seen in argyria.

It is believed that the characteristic brown discoloration of the skin is due to melanin pigmentation. Melanin is the substance which is formed for example when a caucasian develops a suntan. Thus, it is believed that post-inflammatory hyperpigmentation is a condition where the skin develops sort of a "mini-suntan" in the areas affected by trauma. Also, exposure to sunlight accentuates this pigmentation. Generally, this discoloration is not permanent and will dissipate over a period of time from about 1 to 24 months. Since many patients are treated primarily for cosmetic reasons, this time period for removal of the discoloration is, in most cases, unacceptable.

At present, no successful treatment for prevention or reduction of post-inflammatory hyperpigmentation is known to exist. While various compositions containing agents for bleaching melanin pigment are available, these are generally intended for treating surface layers of skin, such as, for example, treating sunburn. These compositions are somewhat successful for treatment of surface tissue, but are completely ineffective for treating hyperpigmentation of subsurface layers. The present invention, however, resolves this problem by providing compositions and methods for the prevention, elimination, or substantial reduction of post-inflammatory hyperpigmentation.

SUMMARY OF THE INVENTION

One embodiment of the invention relates to a composition comprising hydroquinone and an aliphatic sulfoxide of the formula

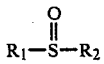

wherein $R_1$ and $R_2$ are alkyl, substituted alkyl, alkenyl, or hetero groups. Although essentially any of these aliphatic sulfoxides are suitable for use in the invention, dimethyl sulfoxide has been found to be particularly advantageous because it is relatively inexpensive and readily available.

It is known that aliphatic sulfoxides in general and particularly dimethyl sulfoxide can increase the permeability of tissue in a reversible manner to enhance the penetration rate of conjointly applied pharmaceuticals. It is not known in this invention, however, whether these sulfoxides act as vehicles or carriers, or whether they act synergistically with the hydroquinone to provide the desired medical effect. What is known, however, is that the combination of sulfoxide and hydroquinone is particularly effective for preventing, eliminating, or substantially reducing post-inflammatory hyperpigmentation.

In any selected dosage form, it is mandatory that the selected sulfoxide be of a pharmaceutically acceptable form. Thus, the sulfoxide must be sufficiently purified so that it does not cause any reaction or injury to the treated subject from contaminants or the like.

Hydroquinone is a well-known pigment bleaching compound which has been used for years in the form of a cream, ointment, or liquid for treatment of surface skin layers. These creams, ointment, or liquid, which are topically administered, are partially effective to various degrees depending upon the specific condition to be remedied. It was found by extensive experimentation that hydroquinone cream by itself is not effective for preventing, eliminating, or substantially reducing post-inflammatory hyperpigmentation.

The mechanism of action for hydroquinone is believed to be an inhibition of the enzymes which convert the amino acid tyrosine to the brown pigment melanin. Melanin is synthesized is cells in the skin which are called melanocytes. Since hydroquinone alone was not effective, it is believed that the hyperpigmentation is formed rather deep in the skin.

The concentration of dimethyl sulfoxide is not critical to the invention, and it can range between about 1 and 99 weight percent of the entire composition. Similarly, the hydroquinone concentration is also not critical, but is generally used in the range of between about 1 and 10 weight percent.

If desired, the compositions of the invention can also include appropriate pharmaceutical diluents, excipients, and/or adjuvants. Particularly useful are hydrophilic, sulfoxide- soluble, or miscible diluents with the preferred diluent being water. Generally, hydrophilic diluents lower the freezing point of the sulfoxide component and thus makes them stable over a wider temperature range.

Compositions in accordance with this invention can be formulated to include a wide variety of dermatologically acceptable ingredients or bases and in a number of physical forms. For example, these compositions can be in liquid or cream form as well as in the form of aqueous emulsions or dispersions.

Other pharmaceutical excipients known to those skilled in the art can be employed alone or in conjuncton with other adjuvants to form advantageous dosage forms of the compositions of this invention.

These compositions may be formulated with thickening agents into highly convenient dosage forms such as ointments, creams, lotions, or the like. They may be formed by incorporating with the sulfoxide and hydroquinone various gelling agents or other viscosity increasers which permit release of the sulfoxide and hydroquinone to the skin upon application. These forms are advantageously employed to lessen the run-off from the skin that may occur with more fluid compositions. More importantly, they also permit more sustained contact of the sulfoxide and hydroquinone with the treated surfaces to result in more accurate and controlled dosing. Accidental spilling and undesired contact with the material can also be minimized with the more viscous formulations.

It is advantageous to use water-dispersible thickening agents (i.e., agents dispersible in water to form a homogenous distribution or solution), such as polyethylene glycols, because they are readily compatible with water or other diluents which way be formulated in these compositions. Also, they may readily be washed from the skin following absorption into the skin of the sulfoxide and hydroquinone. Alternatively, an emulsion base may be employed to impart the desired thickening effect, together with the emollient effect of the lipoid phase of the emulsion base, a better spreading and wetting effect and a retardation of the skin-drying effect of the sulfoxide. When compounded with an emulsion base, the sulfoxide is incorporated in the water phase thereof. Another category of thickening bases which can also be used to impart an emollient effect is provided by sulfoxide-soluble lipoidal thickening agents.

The water-soluble thickening bases may utilize polyethylene glycols of different viscosities, depending upon the desired consistency and concentration of sulfoxide to be incorporated, water-dispersible gums, carboxy vinyl polymers, methyl cellulose, sodium carboxy methyl cellulose, alginates and the like, all of which are well known to those skilled in the art.

The composition incorporating emulsion bases may contain the usual ingredients to provide the base, as for example a fatty alcohol such as cetyl alcohol, and emulsifier such as lauryl sulfate and water. Another base may be formulated by mixing equal weight amounts of stearic acid, cetyl alcohol, triethanolamine, and glycerol monostearate together with water.

The sulfoxide-soluble lipoidal thickening agents, for example lanolin, cocoa butter or glycerol monostearate, may be combined with a diluent and added to the composition in proportions to obtain the desired consistency.

It is also possible to formulate the composition having an increased viscosity by adding to a sulfoxide or sulfoxide/carrier liquid solution, hydroquinone in the form of a cream or ointment. Exact proportions are not critical and the examples provide illustrations of useful combinations.

In a preferred embodiment, the compositions according to the invention comprise dimethyl sulfoxide, hydroquinone, and the appropriate pharmaceutical diluents, excipients, and/or adjuvants described hereinabove. In this embodiment, the composition comprises between about 25 and 90 weight percent dimethyl sulfoxide, and between about 1.5 and 5 weight percent hydroquinone.

Since the compositions of this invention are to be topically applied to human or animal tissue, it is preferable to control the pH range of these compositions to between about 3.5 and 10. Irritation of tissue occurs at pHs below about 3.5 and the stability of certain additives can be adversely affected at pHs above 10. Thus, buffering materials can be used to adjust the pH to the desired range. Examples of such buffers would include glycine, citric acid, and alkali earth metal tartrates, phosphates, succinates, phthalates, or others which are well known to those skilled in the art.

The invention also relates to a number of methods for preventing, eliminating or substantially reducing post-inflammatory hyperpigmentation. One method comprises applying a composition of hydroquinone and an aliphatic sulfoxide of the formula

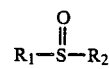

wherein $R_1$ and $R_2$ are alkyl, substituted alkyl, alkenyl, or hetero groups to hyperpigmented tissue of a human or animal subject. In this method, the aliphatic sulfoxide is advantageously dimethyl sulfoxide for the reasons stated hereinabove. Also, the compositions used in this method may also include appropriate pharmaceutical diluents, excipients, and/or adjuvants, if desired.

This method can utilize compositions of various concentrations. For example, the dimethyl sulfoxide component can range between about 1 and 99 weight percent, and the hydroquinone component can range between about 1 and 10 weight percent. If necessary to accelerate treatment, or if otherwise desired, the composition of this method can be repeatedly applied to said hyperpigmented tissue as often as necessary to prevent, eliminate or substantially reduce the post-inflammatory hyperpigmentation.

In a preferred embodiment, a method for preventing, eliminating, or substantially reducing post-inflammatory hyperpigmentation is provided wherein a composition of hydroquinone, dimethyl sulfoxide, and appropriate pharmaceutical diluents, excipients, and/or adjuvants is applied to hyperpigmented tissue of a human or animal subject as often as necessary to eliminate, prevent, or substantially reduce the post-inflammatory hyperpigmentation. In this method, the dimethyl sulfoxide concentration can range between about 25 and 90 weight percent, while the hydroquinone concentration ranges between about 1.5 and 5 weight percent.

These methods may be repeated once or twice daily, or even more frequently, until the hyperpigmentation begins to fade. For some indications (i.e.—certain acute situations), only one or two applications may be sufficient, while in chronic situations, a greater number of or more frequent applications may be necessary.

Accordingly to these methods, the compositions should be topically administered locally to the hyperpigmented area to achieve its maximum effect. "Topical" is intended to include application to all external membrane barriers or tissue which may exhibit the post-inflammatory hyperpigmentation.

In another embodiment of the invention, relating to the treatment for the removal of varicose veins, a method for the prevention, elimination, or substantial reduction of post-inflammatory hyperpigmentation is described. After the varicose veins are removed, a composition of hydroquinone and an aliphatic sulfoxide of the formula

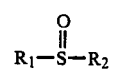

wherein $R_1$ and $R_2$ are alkyl, substituted alkyl, alkenyl or hetero groups is applied to hyperpigmented tissue of a human subject to prevent, eliminate, or substantially reduce the post-inflammatory hyperpigmentation. In this method, a preferred aliphatic sulfoxide is again dimethyl sulfoxide, and the composition can also include appropriate pharmaceutical diluents, excipients, and/or adjuvants. The dimethyl sulfoxide concentration can range between about 1 and 99 weight percent, and the hydroquinone concentration can range between about 1 and 10 weight percent. According to this method the composition can be repeatedly applied as often as necessary to prevent, eliminate, or substantially reduce said post-inflammatory hyperpigmentation.

A preferred method for the prevention, elimination, or substantial reduction of post-inflammatory hyperpigmentation which appears during the treatment for the removal of varicose veins after the varicose veins are removed comprises applying a composition of hydroquinone, dimethyl sulfoxide, and appropriate pharmaceutical diluents, excipients, and/or adjuvants. In this embodiment, the dimethyl sulfoxide advantageously ranges between about 25 and 90 weight percent, and the hydroquinone content ranges between about 1.5 and 5 weight percent.

The invention also relates to a method for the prevention, elimination, or substantial reduction of post-inflammatory hyperpigmentation which appears during the treatment for sloughs, as the slough is healing, and comprises applying a composition of hydroquinone, dimethyl sulfoxide, and appropriate pharmaceutical diluents, excipients and/or adjuvants. In this method, the dimethyl sulfoxide content can range between about 25 and 90 weight percent, and the hydroquinone content can range between about 1.5 and 5 weight percent.

While the above-described compositions and methods are in many cases 100% effective for preventing or eliminating post-inflammatory hyperpigmentation, there are certain situations where a small amount of hyperpigmentation (less than about 25% of the original area) remains. It is not known why this small amount of hyperpigmentation cannot be removed.

One possible explanation is that the remaining pigment is stasis pigment, which is believed to be hemosiderin, a well known decomposition product of the metabolism of blood. In the treatment for varicose veins, a small thrombus or blood clot sususally forms when the veins are injected with a sclerosing solution, and it is reasonable to assume that the metabolism of this blood results in some deposition of hemosiderin. Since the compositions of the present invention are not intended to remove hemosiderin, this would explain the remaining hyperpigmentation. The significant and surprising results of the removal or elimination of most of the hyperpigmentation has been received favorably by patients using the compositions of the invention. Also, as mentioned above, in many cases, particularly in the treatment of sloughs, hyperpigmentation removal is 100%.

While it is apparent that the invention herein disclosed is well calculated to fulfill the objects above stated, it will be appreciated that numerous modifications and embodiments may be devised by those skilled in the art, and it is intended that the appended claims cover all such modifications and embodiments as fall within the true spirit and scope of the present invention.

EXAMPLES

Examples

The scope of the invention is further described in connection with the following examples which are set forth for purposes of illustration only and are not to be construed as limiting the scope of the invention in any manner.

Example 1

A composition of 50% dimethyl sulfoxide 50% water (Rimso 50—manufactured by Research Industries) and 4% hydroquinone in a cream base (Solaquin forte, manufactured by Elder Corp.) was prepared by adding the hydroquinone cream to the dimethyl sulfoxide-water mixture until a solution having a muddy consistency was attained. This composition contained about 1-2% hydroquinone and 25-33% dimethyl sulfoxide.

Example 2

A composition silimar to Example 1 was prepared, except that a 50/50 mixture of a 3% hydroquinone aqueous solution (Melanex, manufactured by Neutragena (Corporation) and Rimso 50 was used. This composition contained approximately 1.5% hydroquinone and 25% dimethyl sulfoxide.

Example 3

A composition was made by mixing equal portions of Melanex (3% hydroquinone) with 100% pure dimethyl sulfoxide. This resulting composition contained about 1.5% hydroquinone, 50% dimethyl sulfoxide.

Example 4

A composition was made by adding pure hydroquinone powder to a 90% dimethyl sulfoxide jelly (manufactured by Interstate Drug Exchange) to form a final a mixture of about 3-5% hydroquinone and about 90% dimethyl sulfoxide.

Example 5

The patient, a 44 year old woman of Italian ancestry, was treated for disfiguring telangiectasias of the legs. Because of her naturally dark complexion, she would have been expected to develop brown pigmentation where the veins were located. The composition of Example 1, estimated to contain about 1.5% hydroquinone and 33% dimethyl sulfoxide, was given to the patient with instructions to shake well and apply twice daily to the areas which exhibited the hyperpigmentation. After a one-month follow-up examination, the patient exhibited only a small amount of black and blue discoloration. The composition was effective in preventing the development of brown pigment corresponding to veins which had been removed.

Example 6

A number of new patients, mostly women between the ages of 25 and 50, were treated in a manner similar to the patient of Example 5, except that the compositions of Example 1, 2, 3, or 4 were used. The results for these patients were equally good with no evidence of hyperpigmentation where veins were removed. In certain patients having chronic deep venous insufficiency with stasis pigmentation, complete removal of all pigmentation was not achieved. The remaining pigmentation in those cases was less than 25% of the original.

This is because stasis pigmentation is believed to be hemosiderin as described hereinabove and the compositions and methods of the invention are not intended to remove hemosiderin pigmentation.

Example 7

Based on the successes with treatments utilizing the compositions of Examples 1-4 on new patients (as described in Examples 5 and 6), similar compositions were recommended to patients who initially began treatment for removal of varicose veins during the previous two years. These patients had a number of old, slowly fading brown pigment streaks. In these patients, each composition was 100% effective in preventing pigmentation with further treatment, thus demonstrating the effectiveness of these compositions in patients with a known tendency to pigmentation.

Example 8

One patient who was given the composition of Example 1 to apply to the areas of her legs where varicose veins had been removed applied it to her face on her own initiative to remove freckles. She indicated that most of her freckles faded substantially, and was very pleased with this result. This is a further indication of the surprising and unexpected results which are obtainable by the compositions and methods of this invention.

Side Effects

Neither hydroquinone nor aliphiatic sulfoxides has any known serious side effects with brief use. With the short-term use advocated in the present examples, two mild side-effects have been observed:

1. Allergy—About one out of thirty patients who apply one of these compositions develops a typical contact dermatitis with intense erythema (redness) and pruritis (itching). This condition rapidly resolves when the hydroquinone-sulfoxide treatment is discontinued.

2. Dryness—These compositions are extremely drying. Patients with dry skin will actually begin to peel after 2-3 weeks, similar to the effects of a sunburn. After discontinuing the application of the composition the peeling would cease, and the new layer of skin beneath the peeling skin was observed to be entirely normal.

Having thus described our invention, what I claim as new and desire to secure by Letters Patent is:

1. A method for preventing or reducing the formation of post-inflammatory hyperpigmentation which comprises applying a composition of between about 1 and 10 weight percent hydroquinone and between about 10 and 90 weight percent of dimethyl sulfoxide to inflamed tissue of a human or animal subject.

2. The method according to claim 1 wherein said composition is applied to said inflamed tissue once or twice daily.

3. A method for preventing or reducing eliminating, or substantially reducing the formation of post-inflammatory hyperpigmentation which comprises applying a composition of between about 1.5 and 5 weight percent hydroquinone, between about 25 and 90 weight percent of dimethyl sulfoxide, and, optionally, pharmaceutical diluents and/or water or sulfoxide soluble thickening agents to inflamed tissue of a human or animal subject once or twice daily to prevent or reduce the formation of said post-inflammatory hyperpigmentation.

4. A method for the prevention, or substantial reduction, of the formation of postinflammatory hyperpigmentation which appears after a treatment for the removal of varicose veins or telangiectasias which comprises applying a composition of between about 1 and 10 weight percent hydroquinone and between about 10 and 90 weight percent of dimethyl sulfoxide to the treated area of a human subject once or twice daily to prevent or substantially reduce eliminate, or substantially reduce the formation of said post-inflammatory hyperpigmentation.

5. The method according to claim 4 wherein said composition further comprises pharmaceutical diluents, or water or sulfoxide soluble thickening agents.

6. A method for the prevention or substantive reduction the formation of post-inflammatory hyperpigmentation which appears after treatment for the removal of varicose veins or telangiectasias which comprises applying a composition of between about 1.5 and 5 weight percent hydroquinone, between about 25 and 90 weight percent dimethyl sulfoxide, and pharmaceutical diluents and/or water once or twice daily to the treated area of a human subject to prevent or substantially reduce the formation of said post-inflammatory hyperpigmentation.

* * * * *